(12) United States Patent
Frederick et al.

(10) Patent No.: US 7,749,278 B2
(45) Date of Patent: Jul. 6, 2010

(54) METHOD OF IMPLANTING USING A SET OF FEMORAL PROSTHESES

(75) Inventors: Philip Frederick, Memphis, TN (US);
David C. Kelman, Collierville, TN (US); Vince Shotton, Magnolia, TX (US)

(73) Assignee: Smith & Nephew, Inc., Memphis, TN (US)

( * ) Notice: Subject to any disclaimer, the term of this patent is extended or adjusted under 35 U.S.C. 154(b) by 99 days.

(21) Appl. No.: 11/415,525

(22) Filed: May 2, 2006

(65) Prior Publication Data
US 2007/0112433 A1 May 17, 2007

Related U.S. Application Data

(60) Provisional application No. 60/679,283, filed on May 9, 2005.

(51) Int. Cl.
*A61F 2/32* (2006.01)
(52) U.S. Cl. .................. 623/22.41; 623/23.44; 623/908
(58) Field of Classification Search .............. 623/22.41, 623/23.15, 23.18, 23.35, 19.11, 19.14, 23.44, 623/908
See application file for complete search history.

(56) References Cited

U.S. PATENT DOCUMENTS

| | | | | |
|---|---|---|---|---|
| 3,547,115 A | * | 12/1970 | Stevens | 606/86 |
| 4,164,793 A | * | 8/1979 | Swanson | 623/21.14 |
| 4,310,931 A | | 1/1982 | Muller | |
| 4,753,657 A | * | 6/1988 | Lee et al. | 623/16.11 |
| 4,908,035 A | | 3/1990 | Deckner et al. | |
| 5,108,451 A | * | 4/1992 | Forte | 623/22.41 |
| 5,152,799 A | * | 10/1992 | Lyons | 623/23.32 |
| 5,211,666 A | * | 5/1993 | Fetto | 623/23.28 |
| 5,314,492 A | | 5/1994 | Hamilton et al. | |
| 5,480,449 A | | 1/1996 | Hamilton et al. | |
| 5,658,352 A | | 8/1997 | Draenert | |
| 6,221,110 B1 | * | 4/2001 | Copf | 623/22.21 |

(Continued)

FOREIGN PATENT DOCUMENTS

DE 19740755 A1 * 3/1999

(Continued)

OTHER PUBLICATIONS

Noble, et al., 'The Geometry of the Proximal Femur and the Design of Hip Endoprostheses,' *Technical Principles, Design and Safety of Joint Implants*, pp. 111-122, Hogrefe & Huber, Lewiston, New York (1994).

*Primary Examiner*—Brian E. Pellegrino
(74) *Attorney, Agent, or Firm*—Kilpatrick Stockton LLP

(57) ABSTRACT

Orthopaedic implants, orthopaedic implant sets, and/or methods for making the same. Aspects and embodiments of the present invention may include orthopaedic implants having an elongated insertion region including proximal, distal, and transition portions, wherein at least portions of at least one face each of the proximal and transition portions are defined by spaced apart constant radii of curvature. The same or other aspects and embodiments may include sets of orthopaedic implants in which proximal portions of the implants grow at different rates than distal portions of the implants. The same or other aspects and embodiments may include methods for making implants and/or sets of implants by studying the geometries of differently sized bony anatomies.

11 Claims, 13 Drawing Sheets

U.S. PATENT DOCUMENTS

| | | |
|---|---|---|
| 6,224,634 B1 * | 5/2001 | Keller .................. 623/23.15 |
| 6,436,147 B1 * | 8/2002 | Zweymuller ............ 623/22.41 |
| 6,443,992 B2 | 9/2002 | Lubinus |
| 6,613,094 B2 | 9/2003 | Zweymuller |
| 6,783,553 B2 | 8/2004 | Grimes |
| 6,942,702 B2 | 9/2005 | Mitsugi et al. |
| 2002/0007220 A1 | 1/2002 | Gie et al. |
| 2005/0055103 A1 * | 3/2005 | Badatcheff et al. ....... 623/22.42 |
| 2005/0267586 A1 * | 12/2005 | Sidebotham ............ 623/22.41 |
| 2005/0278031 A1 * | 12/2005 | Tornier et al. ............ 623/19.12 |

FOREIGN PATENT DOCUMENTS

| | | |
|---|---|---|
| GB | 2 268 064 A | 1/1994 |

* cited by examiner

METHOD OF IMPLANTING USING A SET OF FEMORAL PROSTHESES

RELATED APPLICATIONS

This document claims the benefit of U.S. Provisional Application Ser. No. 60/679,283, entitled "Hip Femoral Implant" and filed May 9, 2005, the entire contents of which are incorporated by this reference.

RELATED FIELDS

Aspects and embodiments of the present invention relate to one or more orthopaedic implants as well as methods for making one or more orthopaedic implants.

BACKGROUND

Orthopaedic implants, such as femoral implants, tibial implants, humeral implants, or others, can be installed in or otherwise associated with the bony anatomy for treating traumatic injuries, reconstructing joint function, or for other purposes. Such implants may include an elongated insertion region, such as the stem region of a femoral hip implant, which can be at least partially inserted into the medullary canal of the proximal femur.

In some instances, the success of the orthopaedic implant may depend on how well the elongated insertion region fits into the bony anatomy. For example, with a femoral hip stem, it is important that proximal portions of the elongated insertion region fit tightly into the medullary canal, such that the stem loads proximal portions of the femur, preventing bone loss through stress shielding and/or resorption (and potentially subsequent failure of the implant). It is also important that distal portions fit snugly into the medullary canal; however, the fit should not be so tight as to prevent proximal loading.

A good fit between the orthopaedic implant and its associated bony anatomy may also help to prevent or lessen micromotion between the implant and the bone. Excessive micromotion may also lead to implant failure.

Because bone geometries vary from person to person (and may also vary with age), typical orthopaedic implants are often offered as part of a set or series of different sized implants. Typically, implant sets are created by first designing one size of implant and then scaling that implant in a proportional manner to define the geometries of the other implant sizes (e.g., increasing the width of the elongated insertion region by a uniform amount along the entire length of the stem).

Typical implant system growth does not accurately reflect the geometries of different bone sizes. Larger femurs, for example, are not simply bigger versions of smaller femurs. For instance, it has been discovered that proximal portions of the medullary canal (some or all of which may be referred to as the metaphysis) may "grow" at a greater rate than distal portions (some or all of which may be referred to as the diaphysis) as femoral size increases. Thus, femoral hip stem sets that grow the proximal portion at the same rate as the distal portion from size to size do not necessarily reflect the actual geometries of the various sizes of femurs. Thus, implant sets made in accordance with traditional methodologies may, in some cases, fit poorly when installed, and may lead to implant failure for the reasons discussed above or for other reasons.

SUMMARY

Various aspects and embodiments of the present invention may provide for orthopaedic implants that more accurately reflect the actual geometries of the various sizes of bony anatomies (such as the various sizes of femurs, tibias, humeri, or other bones).

In accordance with some embodiments, an implant may include an elongated insertion region for implanting into a medullary canal of the bony anatomy. The elongated insertion region may include a proximal portion and a distal portion. The proximal portion may be designed and may include geometries to have a desired fit in corresponding proximal portions of the medullary canal (such as, in some embodiments, the metaphysis). Similarly, the distal portion may be designed and may include geometries to have a desired fit in corresponding distal portions of the medullary canal (such as, in some embodiments, the diaphysis). In accordance with these or other embodiments, the proximal and distal portions may be connected by a transition portion (which may or may not include one or more faces defined by a constant radius of curvature) that facilitates an at least somewhat smooth transition between the proximal and distal portion geometries.

Various aspects and embodiments of the present invention may also include methodologies for making the above-described orthopaedic implants, or other orthopaedic implants. In accordance with some embodiments, such methodologies may include defining geometries for at least parts of the proximal and distal portions of a first orthopaedic implant by using data relevant to one or more bony anatomies appropriate for the general size of the first orthopaedic implant size. In accordance with these or other embodiments, such methodologies may further include defining geometries for at least parts of the proximal and distal portions of a second orthopaedic implant by using data relevant to one or more bony anatomies appropriate for the general size of the second orthopaedic implant.

Orthopaedic implants, including implant sets, created using the above methodologies, or other methodologies, in accordance with certain aspects and embodiments of the present invention, may include at least some implants that do not "grow" uniformly with respect to other implant sizes. For example, in accordance with certain aspects and embodiments of the present invention, orthopaedic implant sets may include some implant sizes in which proximal portions of the implant's elongated insertion region increases to a greater degree than distal portions of the elongated insertion region with respect to a smaller implant size.

These, and other aspects and embodiments of the present invention are described in more detail in the remainder of this document.

DETAILED DESCRIPTION OF DRAWINGS

Figure 1:
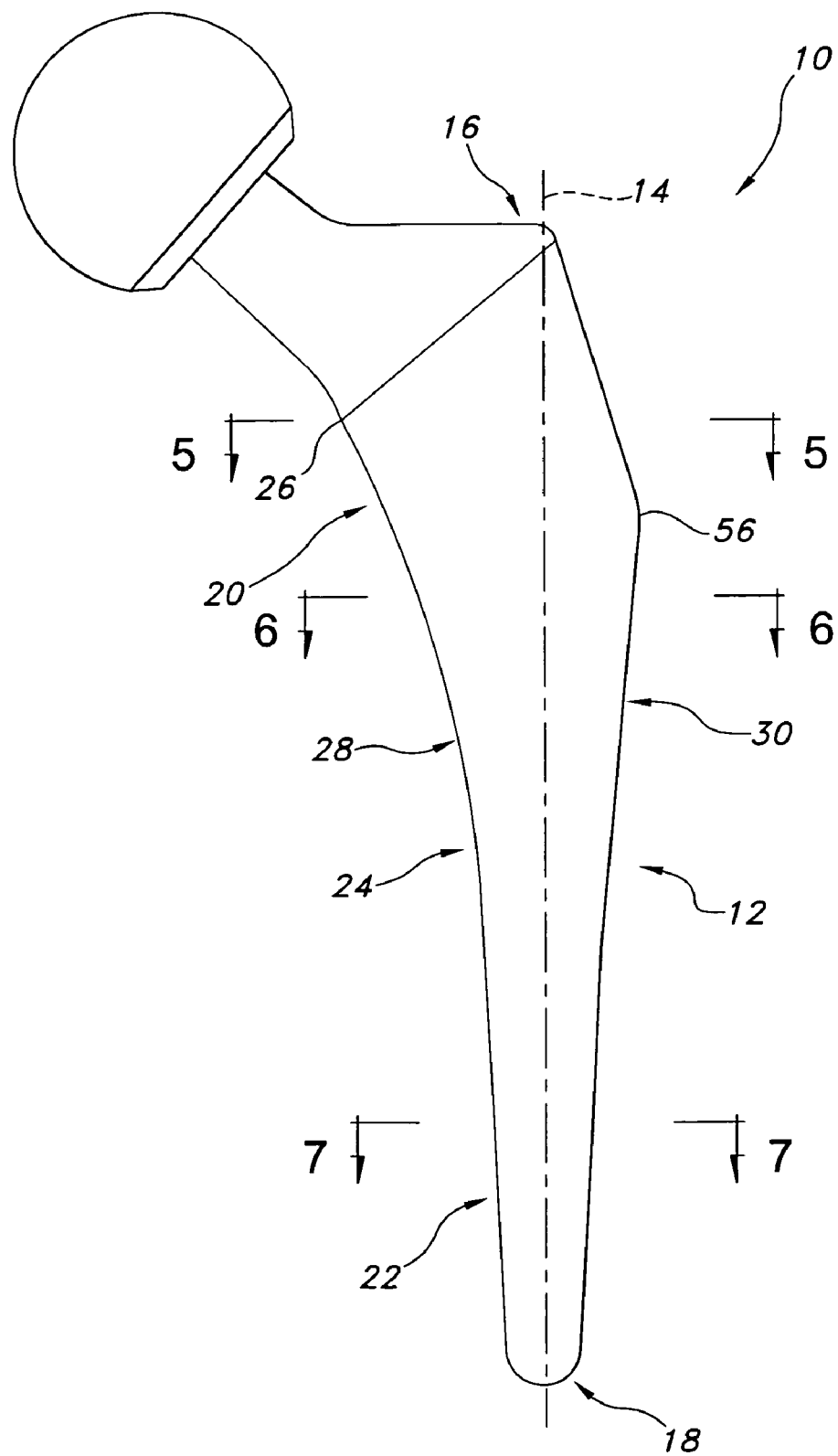
FIG. 1 is an anterior view of an orthopaedic implant in accordance with one embodiment of the present invention.

FIG. 1 shows an orthopaedic implant 10 in accordance with certain aspects and embodiments of the present invention. As shown in FIG. 1, orthopaedic implant 10 may include an elongated insertion region 12. Elongated insertion region 12 may facilitate installing orthopaedic implant 10 in, or otherwise associating orthopaedic implant 10 with, the bony anatomy. For example, in some embodiments, elongated insertion region 12 may be at least partially inserted into a prepared or natural medullary canal of the bony anatomy.

The orthopaedic implant 10 shown in FIG. 1 is a femoral hip stem for implantation into the medullary canal of a femur. The present invention, however, is not limited to femoral hip stems. Other aspects and embodiments of the present invention may include other femoral implants (including implants for the proximal, mid, and/or distal regions of the femur), tibial implants, humeral implants, other implants for the medullary canal, or other types of orthopaedic implants for installation in or association with the bony anatomy. Thus, although the accompanying Figures and the below description illustrate a femoral hip stem embodiment, other types of implants are within the scope of the present invention.

Figure 2:
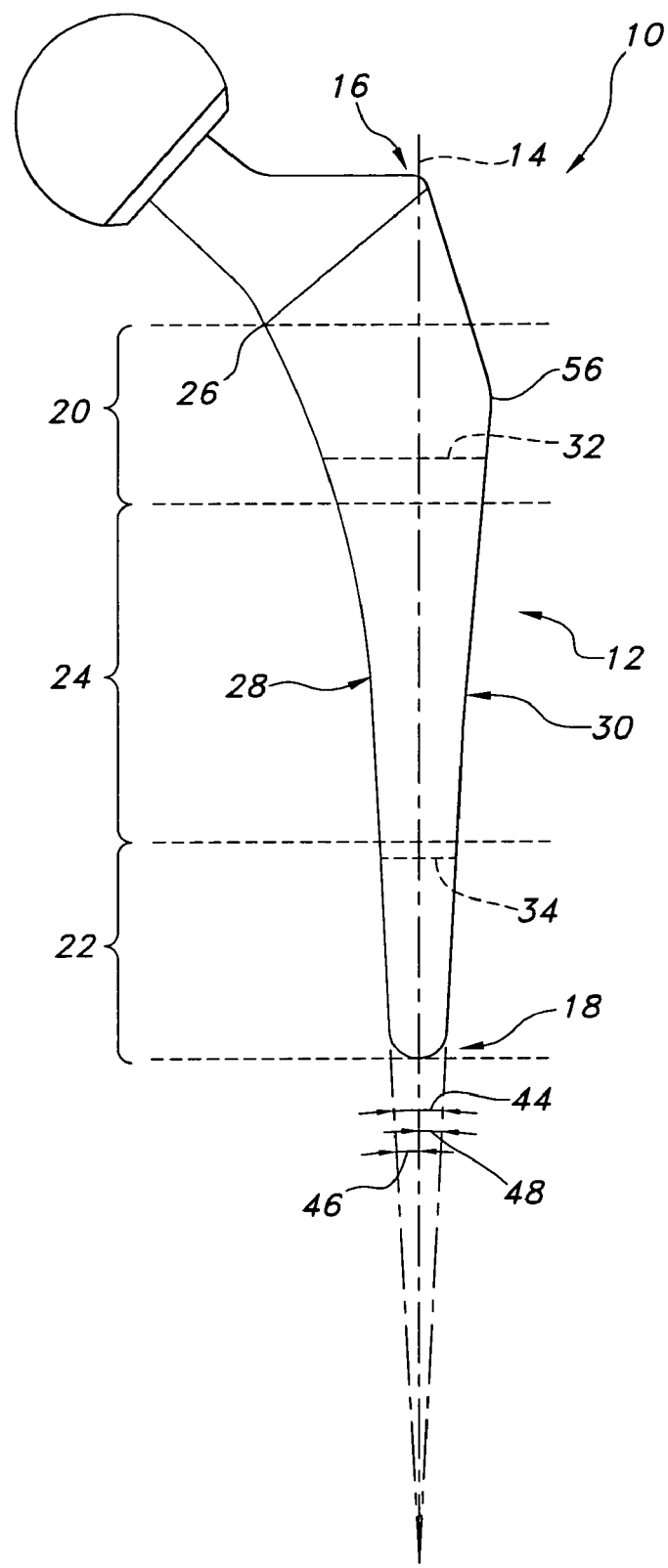
FIG. 2 is another anterior view of the orthopaedic implant of FIG. 1, illustrating various geometries of the implant.
Figure 3:
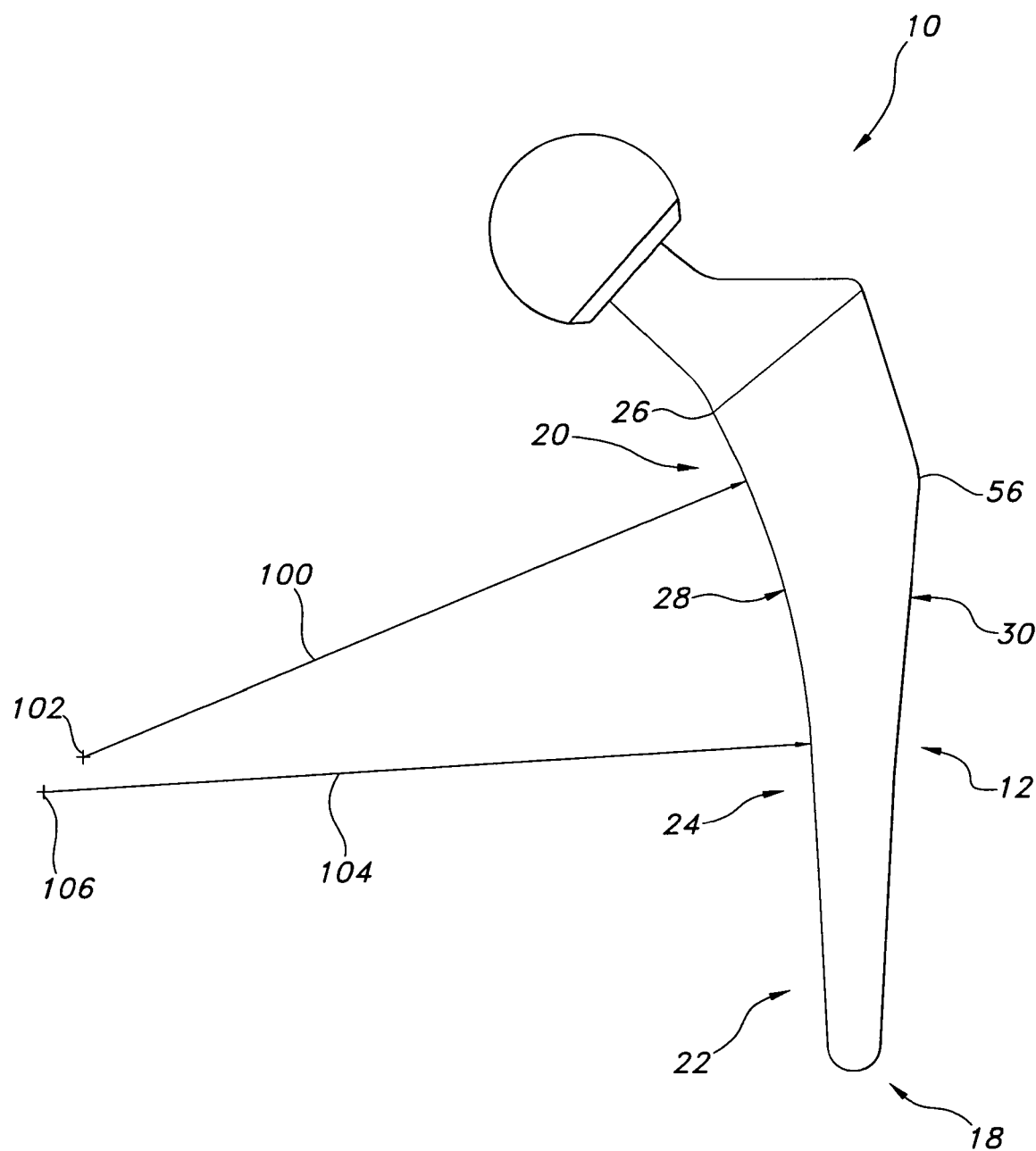
FIG. 3 is another anterior view of the orthopaedic implant of FIG. 1, illustrating additional geometries of the implant.
Figure 4:
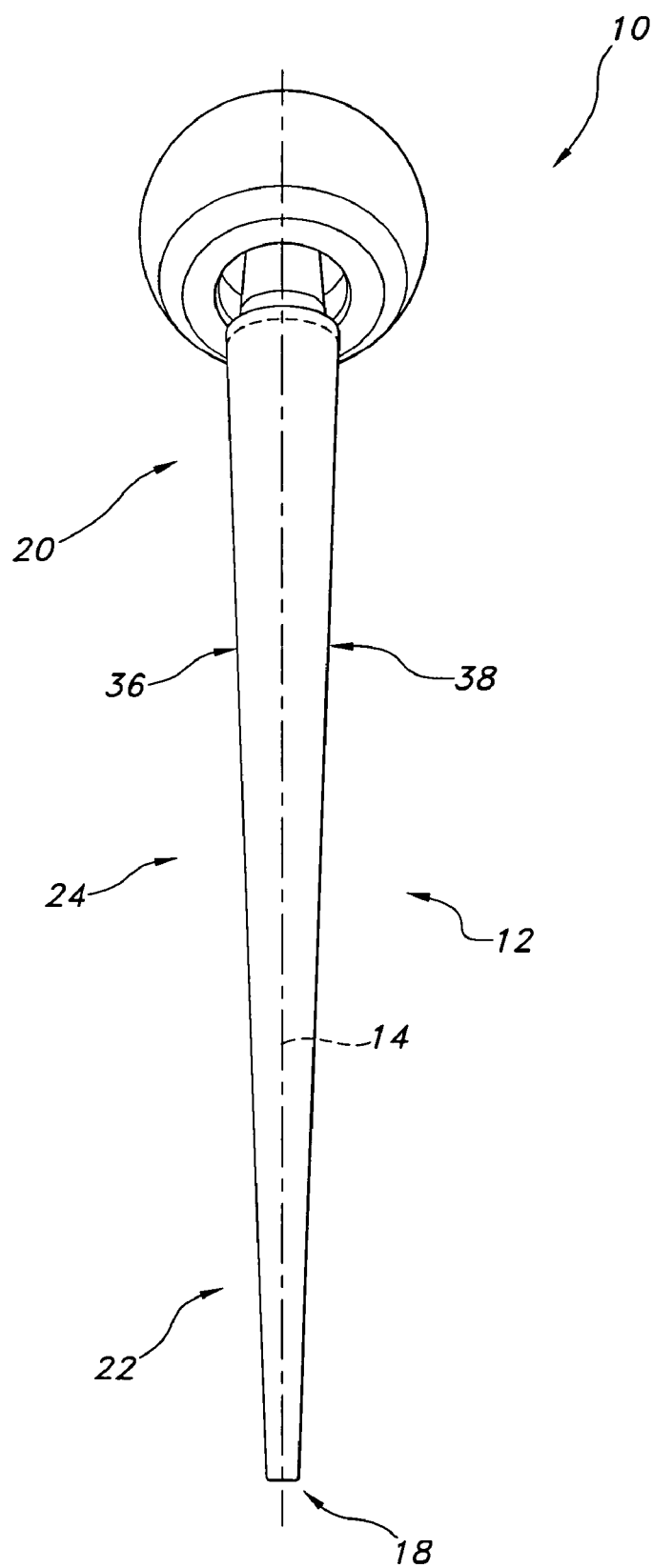
FIG. 4 is a lateral view of the orthopaedic implant of FIG. 1.

FIGS. 1-3 schematically illustrate some of the implant's 10 geometries. In these or other embodiments, however, additional or alternative measurements and constructs may be used to define the geometries of the implant.

In the embodiments of FIG. 1, orthopaedic implant 10 defines a longitudinal axis 14. As shown, longitudinal axis 14 generally extends between an upper portion 16 and a distal tip 18 of the implant 10 and may roughly correspond to a anatomic axis of the bony anatomy for which the implant 10 is intended. It is not necessary, however, that longitudinal axis 14 extend between upper portion 16 and distal tip 18, or that longitudinal axis correspond to the bony anatomy's mechanical axis. In accordance with this or other embodiments of the present invention, orthopaedic implant 10 may define other longitudinal axes, which may or may not extend between the upper portion 16 and distal tip 18 and which may or may not extend along the mechanical axis of the bony anatomy for which the implant 10 is intended.

In the embodiments of FIG. 2, the elongated insertion region 12 is divided into a proximal portion 20, a distal portion 22, and a transition portion 24. The proximal portion 20 shown extends from an osteotomy point 26 to the proximal end of transition portion 24, the transition portion 24 shown extends from the distal end of proximal portion 20 to the proximal end of distal portion 22, and the distal portion 22 shown extends from the distal end of transition portion 24 to the implant's distal tip 18. In accordance with other aspects and embodiments of the present invention, however, the proximal, distal and transition portions (20, 22 and 24) may overlap and/or are not necessarily defined by distinct boundaries. In still other embodiments, elongated insertion region 12 does not include a transition portion 24, and the proximal portion 20 may extend up to or overlap the distal portion 22. In still other embodiments, the proximal and distal portions 20 and 22 may be reversed from the orientations shown in FIG. 2.

As discussed above, in some embodiments, the osteotomy point 26 indicates the proximal end of the proximal portion 20. The osteotomy point 26 may roughly correspond to the point where a resection plane (in this embodiment, a proximal femur resection plane) intersects the implant's medial face 28 when implanted. In other embodiments, the proximal portion 20 may be defined with respect to other structures or features of the prepared or unprepared bony anatomy and/or the implant 10 itself, and the implant 10 does not necessarily include an osteotomy point 26.

In the embodiments shown in FIG. 3, a constant radius of curvature 100 extends from center 102 and defines the curve or arc of the medial face 28 in the proximal portion 20, and a second constant radius of curvature 104 extends from center 106 and defines the curve or arc of the medial face 28 in the transition portion 24. Radii of curvature 100 and 104 may be different, or the same, lengths. In the embodiments shown in FIG. 3, centers 102 and 106 are spaced apart from one another, although, in other embodiments, they may be the same.

In accordance with some of the embodiments of the present invention, the arcs defining the medial face, including the proximal portion 20 medial face, transition portion 24 medial face, or any other portions and/or faces need not be defined by a constant radius of curvature. Instead, they can, in these or other embodiments, track parabolic paths, hyperbolic paths, elliptical sections, and/or can be any desired curved shape. Thus, the medial faces of the proximal portion 20 and the transition portion 24 (and any other portion) may be curves or arcs defined in any desired manner. For example, the medial faces of proximal and transition portions 20 and 24 may be defined by a parabolic equation or another geometric or non-geometric equation instead of comprising part of a circle. In still other embodiments, the medial faces of proximal and transition portions 20 and 24 are not subject to empirical definition by a mathematic equation.

In other embodiments, the proximal portion 20 and the transition portion 24 of the medial face 28 may be both defined by a single radius of curvature extending from a single center. In still other embodiments, the proximal portion 20, the distal portion 22, and the transition portion 24 of the medial face 28 may be all defined by a single radius of curvature extending from a single origin. In still other embodiments, neither the proximal portion 20, nor the distal portion 22, nor the transition portion 24 are defined by a constant radius of curvature.

In accordance with the embodiments illustrated in FIGS. 1-3, the proximal portion 20 may generally correspond to the metaphysis and the distal portion 22 may generally correspond to the diaphysis when the implant 10 is implanted into the femur's medullary canal. In other embodiments, the proximal portion 20, distal portion 22, and/or transition portion 24 may overlap portions of the metaphysis and/or diaphysis of the medullary canal.

In accordance with some of the aspects and embodiments of the present invention, the proximal portion 20 may be about 5 to about 55 millimeters long, the distal portion 22 may be about 5 to about 55 millimeters long, and the transition portion 24 may be about 15 to about 65 millimeters long, although in other aspects and embodiments of the present invention, some or all of these portions may have lengths falling outside these ranges. In accordance with some embodiments, the lengths of the proximal, distal, and/or transition portions may increase as the size of the implant increases.

In the embodiments shown in FIGS. 1-7, the elongated insertion region 12 generally tapers from the proximal portion 20 to the distal portion 22, in both the anterior-posterior widths as well as the medial-lateral widths. In other embodiments, elongated insertion region does not taper in one or both of the anterior-posterior and medial-lateral widths.

The tapered elongated insertion region 12 shown in FIGS. 1-7 defines a plurality of widths, including, but not limited to, proximal portion 20 widths between the medial face 28 and the lateral face 30 of the implant 10 (such as, for example, the medial-lateral proximal portion width 32 shown in FIG. 2), distal portion 22 widths between the medial and lateral faces 28 and 30 (such as, for example, the medial-lateral distal portion width 34 shown in FIG. 2), proximal portion 20 widths between the anterior face 36 and the posterior face 38 of the implant, and distal portion 22 widths between the anterior and posterior faces 36 and 38. Widths 32 and 34 are provided by way of example only. In the embodiments of FIGS. 1-7, because the elongated insertion region 12 includes curved and tapered surfaces, it defines almost an infinite number of widths in both the anterior-posterior and medial-lateral aspects.

Both the proximal widths and the distal widths may be defined in other manners in accordance with other embodiments and aspects of the present invention. For example, proximal, distal and/or transition portion widths could also be defined as the distance between a medial, lateral, anterior, posterior and/or other face of the elongated insertion region 12 and a longitudinal axis of the implant 10 (whether such axis is the longitudinal axis 14 shown in FIG. 1 or another axis).

Figure 5:
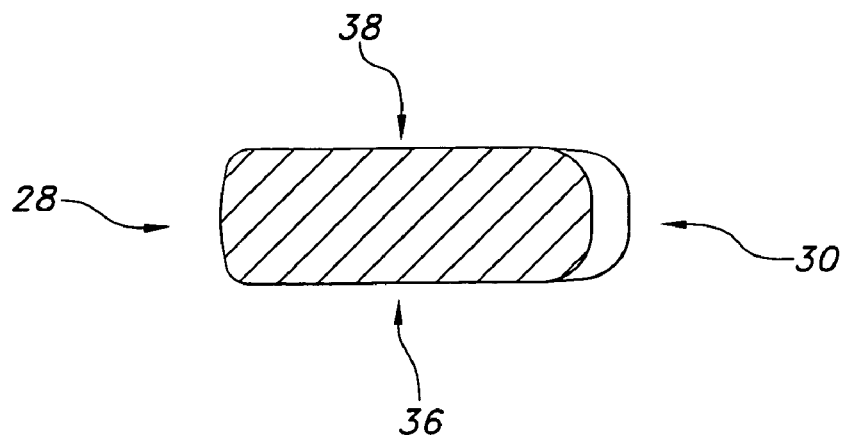
FIG. 5 is a cross-section view of the orthopaedic implant of FIG. 1.
Figure 6:
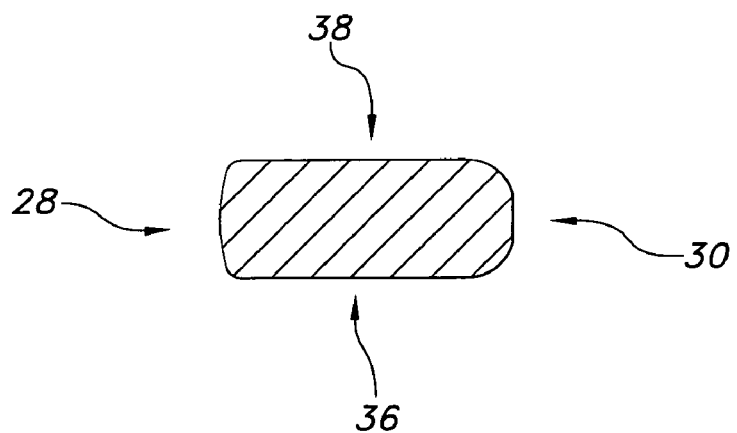
FIG. 6 is also a cross-section view of the orthopaedic implant of FIG. 1.
Figure 7:
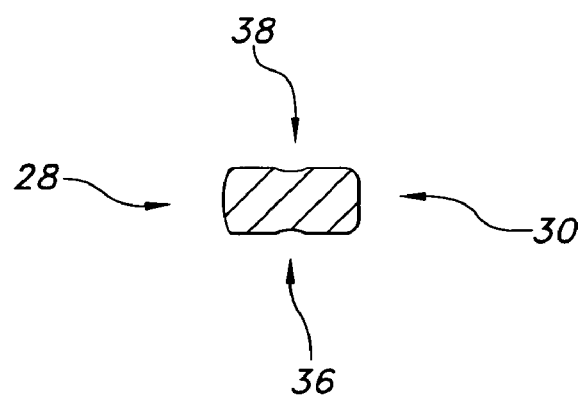
FIG. 7 is also a cross-section view of the orthopaedic implant of FIG. 1.

The embodiments shown in FIGS. 5-7 illustrate portions of elongated insertion region 12 that define a generally rectangular cross section with rounded over corners. The present invention, however, is not limited to orthopaedic implants 10 with rectangular cross sections. In accordance with other aspects and embodiments, elongated insertion regions 10 may define other geometries, including, but not limited to, cylindrical regions, conical regions, fluted regions, slotted regions, and/or other shapes.

In the embodiments shown in FIGS. 1-4, portions of faces 28, 30, 36 and 38 (such as portions of the faces located in distal portion 22 of elongated insertion region 12) and/or longitudinal axis 14 define a number of angles. For instance, in the embodiments shown best in FIG. 2, the medial and lateral faces 28 and 30 of the distal portion 22 define an angle 44. As also shown in FIG. 2, the medial face 28 of the distal portion 22 and the longitudinal axis may define an angle 46.

Similarly, the lateral face 30 of the distal portion 22 may define an angle 48. In these or other embodiments, other faces or surfaces of the elongated insertion region 12 may define other angles (including, but not limited to, anterior and posterior faces 36 and 38 shown in FIG. 4).

In accordance with certain aspects and embodiments of the present invention, the angle 44 between the medial and lateral faces 28 and 30 of the distal portion 22 is approximately six degrees. In these or other embodiments of the present invention the angle 44 is between approximately one and fifteen degrees. In still other embodiments, the angle 44 falls outside the aforementioned range. In some embodiments, angle 44, or other angles, may be varied in accordance with certain implant 10 designs.

As discussed above, in accordance with certain aspects and embodiments of the present invention, some or all of the portions of the elongated insertion region 12 may be shaped and/or sized to provide a desirable fit between the implant 10 and the medullary canal. Various aspects and embodiments of the present invention include methodologies for refining and/or developing implant geometries to provide such a desirable fit.

Figure 8:
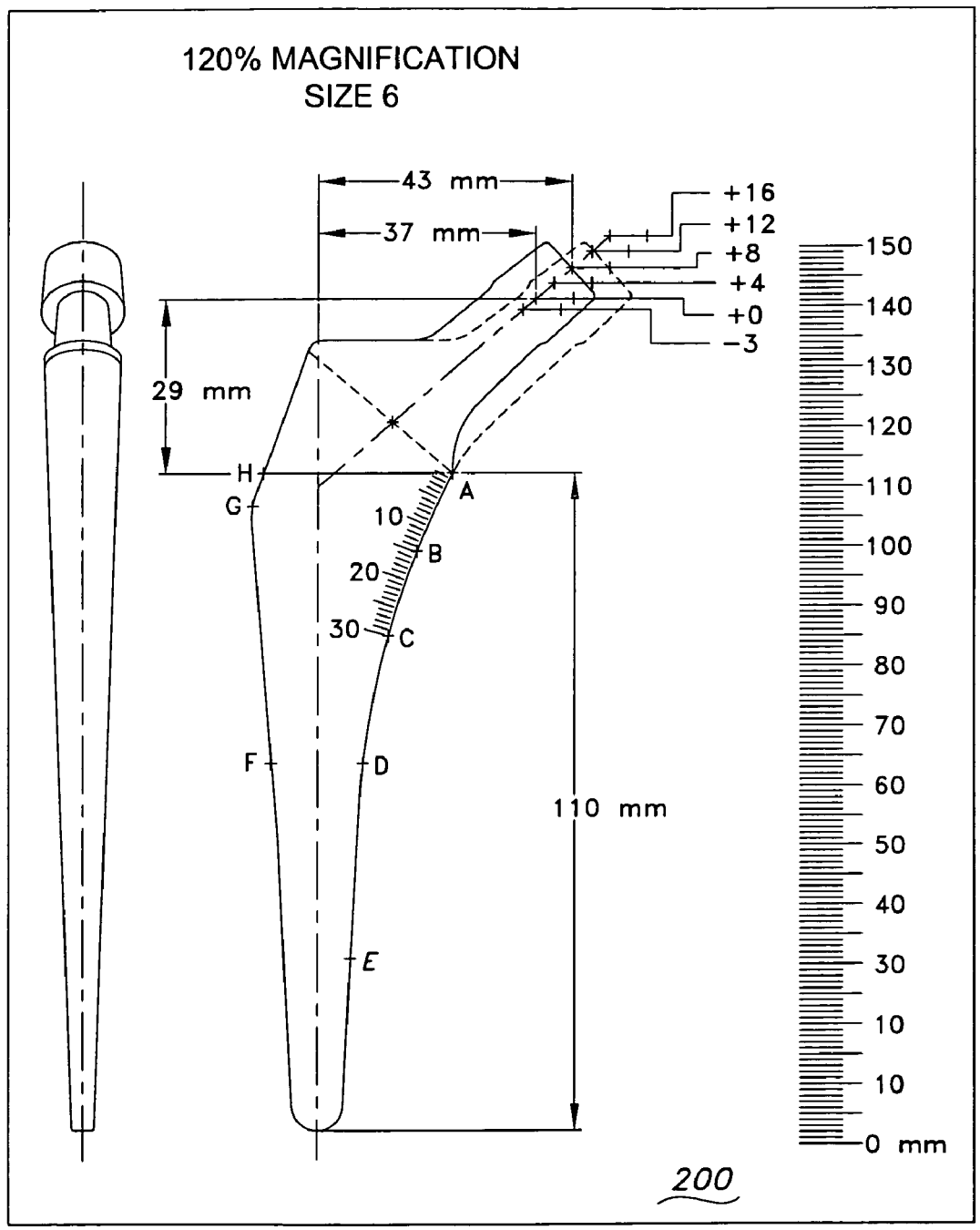
FIG. 8 shows a template in accordance with one embodiment of the present invention.
Figure 9:
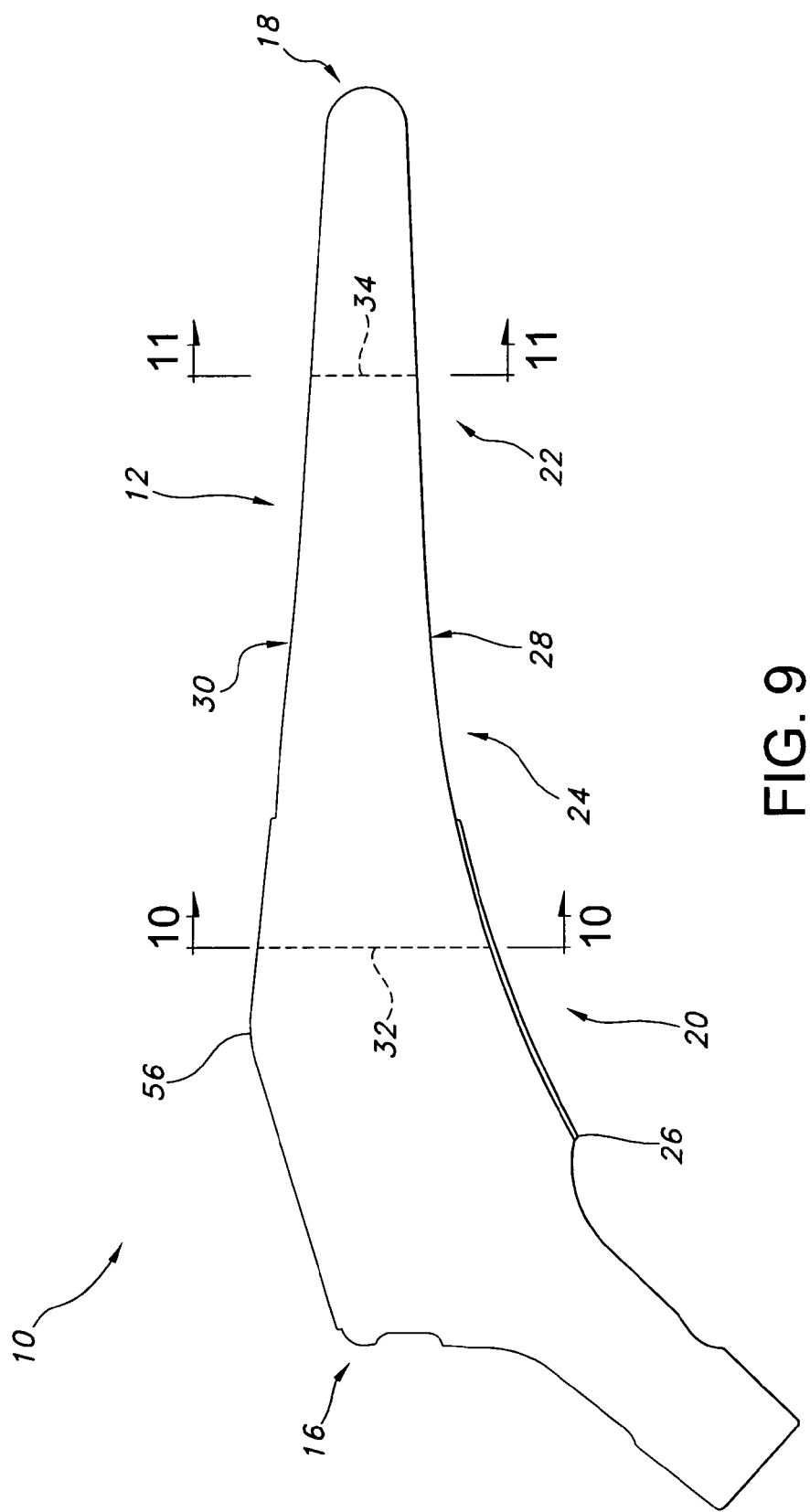
FIG. 9 is an anterior view of the outline of an orthopaedic implant in accordance with one embodiment of the present invention.
Figure 11:
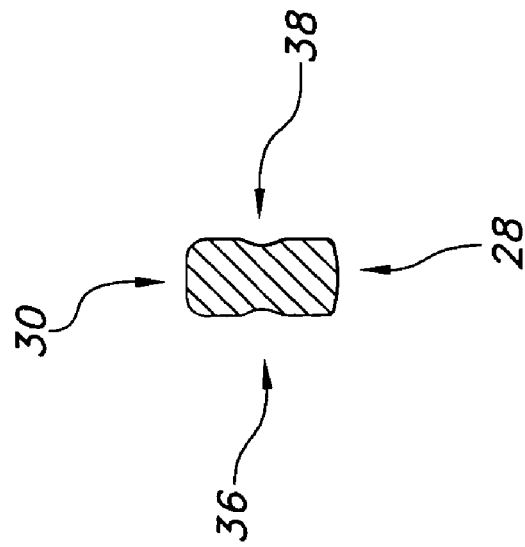
FIG. 11 is also a cross-section view of the orthopaedic implant of FIG. 9.
Figure 10:
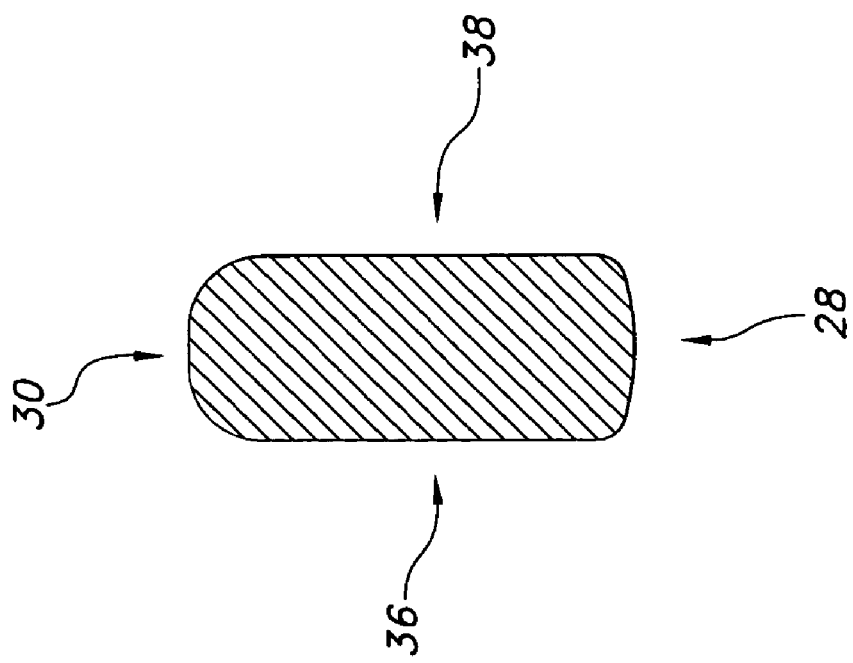
FIG. 10 is a cross-section view of the orthopaedic implant of FIG. 9.
Figure 12:
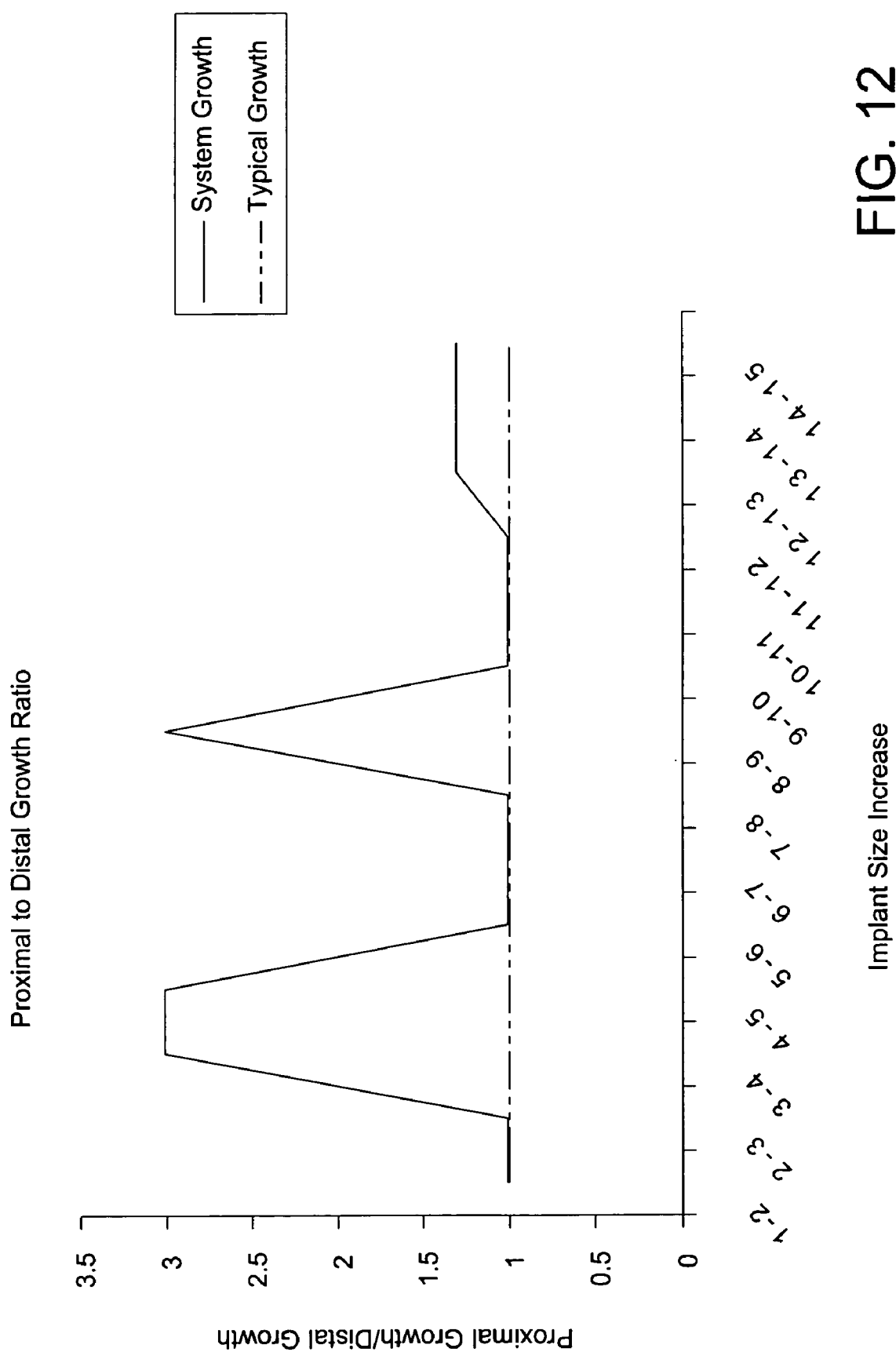
FIG. 12 is a chart plotting proximal/distal growth ratios against implant size increases for a plurality of implants in accordance with one embodiment of the present invention.

FIG. 8 illustrates one methodology for defining at least some of the geometries of the elongated insertion region 12 with some of the aspects and embodiments of the present invention. FIG. 8 shows a template 200 that may be used in conjunction with a templating study to develop and/or refine implant geometries in accordance with certain aspects and embodiments of the present invention. Template 200 may be transparent such that it may be positioned over an x-ray, fluoroscopic or other type of image of the bony anatomy and/or its associated medullary canal. The template 200 shown in FIG. 8 includes an outline of an initial implant geometry 202, from both an anterior view as well as a medial view (although both views are not necessary). In accordance with other embodiments of the present invention, template 200 may include additional or alternative views (including, but not limited to, posterior views, lateral views, and views from other angles or in other planes).

The anterior view shown in FIG. 8 includes a number of reference points (including references A through H) and other constructs for indicating certain geometries and aspects of the initial implant outline. In other embodiments, template 200 may include additional or alternative references and/or constructs to indicate other geometries. As shown in FIG. 8, the template 200 may also indicate what image magnification and the relevant implant size the template 200 is intended for, although such indications are not necessary in all embodiments. The same, or additional, templates may be modified for use with other implant sizes.

Using one or more templates (such as the template 200 shown in FIG. 8), suitable geometries for one or more orthopaedic implants 10 may be defined (including, but not limited to, a set of implants including a plurality of sizes). For example, in some embodiments, one may use the template to evaluate whether the initial implant outline defines implant geometries suitable for the structures of the bony anatomy (such as the metaphysis and diaphysis of the medullary canal) shown in the images.

If the initial implant outline geometries are not suitable, it may be indicated (on the template itself, on another form, or in some other format or medium) how the initial implant outline could be modified to define a better-fitting implant. For example, if the proximal width at reference B did not indicate that such an implant would fit properly in the bony anatomy, it could be noted that reference B needs to move medially or laterally by a certain amount. By recording such discrepancies with respect to these, or other reference points or constructs, it can be recorded how the initial implant outline could be modified to define a better-fitting implant.

In accordance with certain aspects and embodiments of the present invention, the templating study process can be repeated several times with other bony anatomies of the same general size. The accumulated data may be subsequently averaged or otherwise processed to calculate or otherwise determine what changes should be made to the initial implant outline to define a better-fitting implant. In some embodiments, the data could be used to create a second initial implant outline, for a second templating study to further refine the geometries of the implant.

In accordance with some embodiments, such a templating study could be repeated numerous times for various implant and bony anatomy sizes to develop a set or series of implants.

Implant sets, in accordance with some aspects and embodiments of the present invention, do not include implants chosen from unrelated groups of implants, but rather, may include a group of implants sharing common characteristics or traits, but offered in a number of different sizes. Such common characteristics or traits may include, but are not limited to, material properties, mechanical properties, indications for use, trade name or product grouping, geometric properties (such as, but not limited to, stem shapes, neck shapes, neck offsets, etc. . . . , features (such as, but not limited to, fluting, distal slots, presence or absence of bone in growth material, or other features), or other common characteristics or traits or combinations of characteristics or traits.

In accordance with aspects and embodiments of the present invention, methodologies other than a templating study may be used to define suitable implant 10 geometries. For example, in some embodiments, previously collected data on bony anatomy geometries (such as internal widths of various portions of the medullary canal) may be used to calculate or otherwise determine suitable geometries for portions of elongated insertion region 12. In still other embodiments, digitized images of bony anatomy can be processed, with or without the help of computer functionality, to identify suitable geometries for portions of elongated insertion region. Other methodologies may also be employed to identify suitable geometries.

In accordance with some aspects and embodiments of the present invention, data points collected in accordance with one or more of the methodologies discussed above can be used to create one or more orthopaedic implants 10 having elongated insertion regions 12 with desirable bone loading and fixation properties, a more anatomically correct geometry, and/or other desirable features. For example, in accordance with some embodiments, the collected data can be used to define geometries for proximal and distal portions 20 and 22 of the elongated insertion region 12 (such as medial/lateral widths 32 and 34) such that implantation of an appropriate sized implant 10 into the medullary canal of the bony anatomy results in desirable proximal loading of the bone while maintaining a close fit between the distal portion 22 of the elongated insertion region 12 and the corresponding distal portion of the medullary canal.

In accordance with certain aspects and embodiments of the present invention, using one or more of the methodologies discussed above, a combination of those methodologies, or other methodologies, one may define one or more geometries for use in conjunction with an orthopaedic implant 10 or a set or series of such implants 10. In some embodiments, many, if not all, of the geometries of the implant or implants may be defined using such methodologies. In other embodiments, however, in addition to the geometries defined using these methodologies, it may be necessary to develop additional geometries or use traditional geometries to provide the implant manufacturer with sufficient data to construct an implant or an implant set.

For example, in accordance with aspects and embodiments of the present invention, although one or more of the methodologies discussed above may identify geometries for medial/lateral widths 32 and 34 in the proximal and distal portions 20 and 22, it may be too time consuming, or otherwise undesirable, to use such methodologies to define every geometry necessary to construct an implant 10. It may be necessary to also define, for example, anterior/posterior widths in the proximal and distal portions, medial/lateral and/or anterior/posterior widths in the transition portion, angles between the medial face, lateral face and/or longitudinal axes, or other geometries. In such instances, traditional implant 10 geometries may be used, or other techniques may be employed, to supply various geometries not determined through one of the above described methodologies. For example, in one such embodiment, a constant radius 104 extending from center 106 may define the medial face of the transition portion 24. The length and/or center 106 of the radius 104 may be chosen such that it will define a connecting arc between the distal end of the proximal portion 20 and the proximal end of the distal portion 22. In other embodiments, such a methodology is unnecessary and transition portion 24 is either absent (e.g., the distal end of proximal portion 20 abuts the proximal end of distal portion 22) or the medial face of the transition portion 24 is defined in other ways, such as by a parabolic equation or in another manner.

In still other embodiments, the medial face in both the proximal and transition portions 20 and 24 are defined by a single constant radius extending from a center, such that the proximal portion includes the medial/lateral width or widths, defined using a templating study or other methodology but also transitions smoothly into the medial face of the distal portion. In other embodiments, one or more of the angles defined by the distal portion medial face, distal portion lateral face and/or longitudinal axis 14 (or other axes), may be defined and/or adjusted such that the transition(s) between the various portions of the elongated insertion region 12 is/are smooth.

FIGS. 9-16 illustrate a set or series of orthopaedic implants 10 created using some of the methodologies and procedures discussed above in accordance with aspects and embodiments of the present invention. In the embodiments shown in FIGS. 9-16, orthopaedic implants 10 are femoral hip stems and a templating study (using one or more templates similar to the template 200 shown in FIG. 8) was conducted to identify medial/lateral widths 32 (twenty millimeters distal to the osteotomy point 26) located in the proximal portion 20, and also medial/lateral widths 34 (eighty millimeters distal to the osteotomy point 26) located in the distal portion 22, for fifteen sizes of femoral hip stems (arbitrarily numbered 1 through 15).

As shown by the dashed line in FIGS. 12-15, some typical femoral hip stem sets grow uniformly in the proximal and distal regions from size to size (i.e. proximal growth divided by distal growth equals one). Unlike the typical femoral hip stem set illustrated in the Figures, however, the implants 10 made in accordance with embodiments of the present invention do not always grow uniformly in the proximal and distal regions from size to size (proximal growth divided by distal growth does not always equal one, although for some size increases it does). In FIGS. 12-15, the "x" column indicates the medial/lateral width 32 in proximal portion 20, the "y"

column indicates the medial/lateral width 34 in distal portion 22, and the "z" column indicates length of the elongated insertion region 12.

As shown in FIGS. 12-15, growth rates do not have to have to be precisely the same to have a growth ratio of approximately 1. As one example, with reference to the embodiment of FIG. 13, the size 2 implant 10 includes a proximal portion width 32 of 19 mm (at a level about 20 millimeters distal from the osteotomy point 26 level) (which may, in some embodiments, be represented as $PW1_{20\,mm}$) and a distal portion width 34 of 7.4 mm (at a level about 80 millimeters distal from the osteotomy point 26 level) (which may, in some embodiments, be represented as $DW1_{80\,mm}$); whereas the size 3 implant 10 includes a proximal portion width 32 of 20.4 millimeters (at a level about 20 millimeters distal from the osteotomy point 26 level) (which may, in some embodiments, be represented as $PW2_{20\,mm}$) and a distal portion width 34 of 8.9 millimeters (which may, in some embodiments, be represented as $DW2_{80\,mm}$). In this example, the difference between the proximal portion widths 32 of the size 2 and 3 implants 10 is 1.4 millimeters (which may be represented as $PW2_{20\,mm} - PW1_{20\,mm} = \Delta PW_{20\,mm}$) and the difference between the distal portion widths 34 of the size 2 and 3 implants 10 is 1.5 millimeters (which may be represented as $DW2_{80\,mm} - DW1_{80\,mm} = \Delta DW_{80\,mm}$). In this example, the growth rates with respect to the proximal and distal portions is relatively uniform. In other words, in accordance with this embodiment, $\Delta PW_{20\,mm}$ (here, 1.4 millimeters) is substantially equal to $\Delta DW_{80\,mm}$ (here, 1.5 millimeters) and thus the proximal to distal growth ratio shown in FIG. 13 between implant 10 sizes 2 and 3 may be plotted at substantially 1 ($\Delta PW_{20\,mm}$ divided by $\Delta DW_{80\,mm}$) (in this case, about 0.93).

Figure 13:
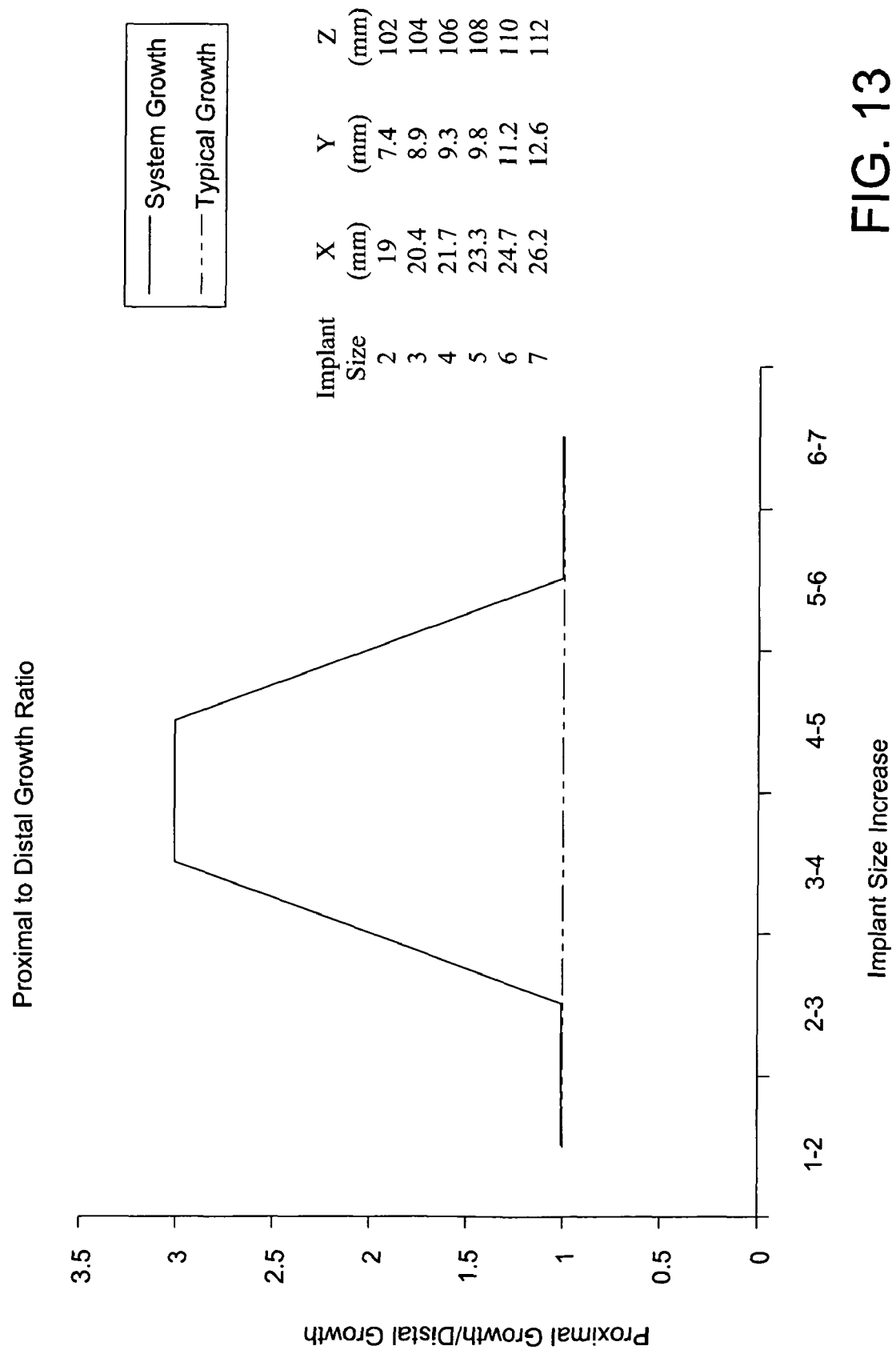
FIG. 13 is a chart providing additional information about the chart of FIG. 12.
Figure 14:
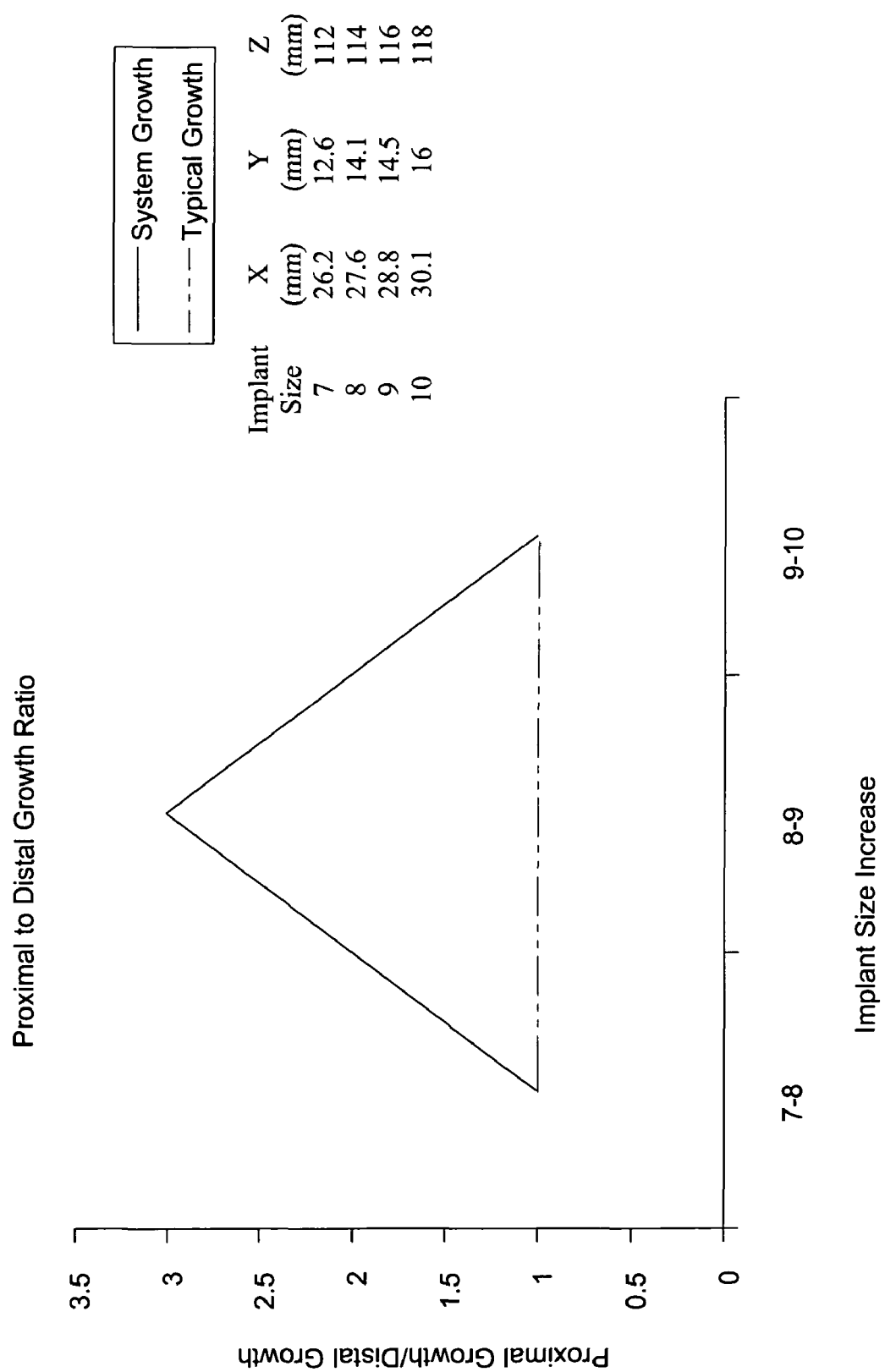
FIG. 14 is also a chart providing additional information about the chart of FIG. 12.
Figure 15:
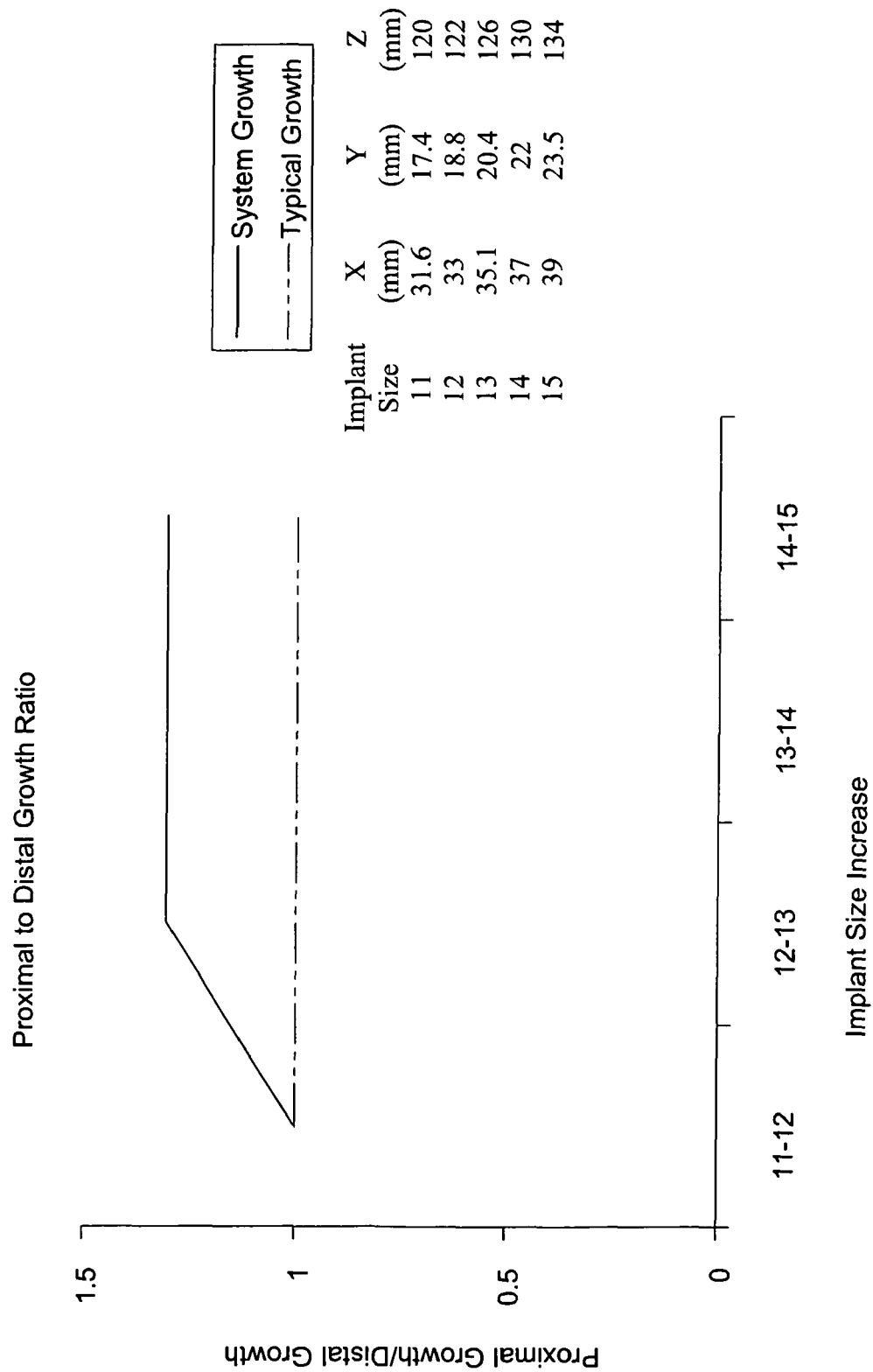
FIG. 15 is also a chart providing additional information about the chart of FIG. 12.

In accordance with the embodiment shown in FIG. 13, however, the proximal to distal growth ratio is not always substantially equal to 1, since the proximal and distal portions of the implant 10 do not always grow in a uniform manner form one size to the next. For example, the size 4 implant 10 includes a proximal portion width 32 of 21.7 millimeters ($PW1_{20\,mm}=21.7$) and a distal portion width 34 of 9.3 millimeters ($DW1_{80\,mm}=9.3$) and thus, with respect to comparing the proximal and distal growth rates of implant 10 sizes 3 and 4, $\Delta PW_{20\,mm}$ equals 1.3 millimeters and $\Delta DW_{80\,mm}$ equals 0.4 millimeters. In this example, the growth rates with respect to the proximal and distal portions is 3.25 and is thus not relatively uniform, ($\Delta PW_{20\,mm}$ is not substantially equal to $\Delta DW_{80\,mm}$ and $\Delta PW_{20\,mm}$ divided by $\Delta DW_{80\,mm}$ is not about 1). The above is offered as an example only, and does not define with mathematical precision the boundaries of "substantially equal."

Figure 16:
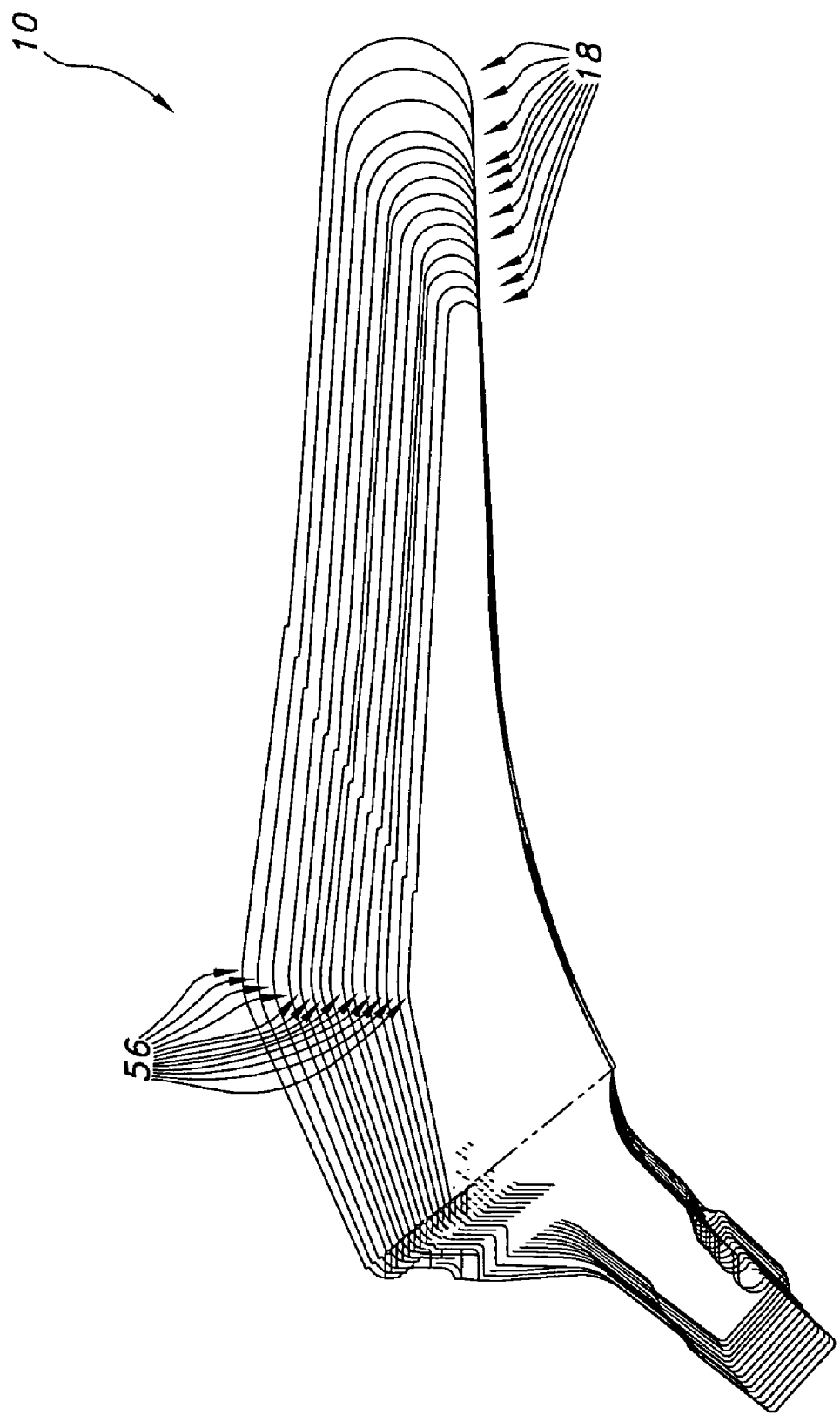
FIG. 16 shows an anterior view of the outlines of a plurality of orthopaedic implants superimposed over one another in accordance with one embodiment of the present invention.

FIG. 16 shows the outlines of the orthopaedic implants 10 of FIGS. 9-15, shown superimposed over one another. As shown in FIG. 16, the medial faces of the various implants 10 align with one another and the "growth" of the implants 10 occurs along the lateral faces of the implants 10. Thus, although not shown in FIG. 16, a single constant radius of curvature extending from a single center may define the medial faces of the proximal portions of the implants 10 and, similarly, a single constant radius of curvature extending from a single center may define the medial faces of the transition portions of the implants 10. Also, as the implants 10 shown in FIG. 16 grow, the shoulders 56 remain substantially aligned throughout the implant's growth, which may facilitate consistency in the location of where proximal fixation occurs throughout the range of implant sizes.

Changes, modifications, additions, and/or deletions may be made to the systems, methodologies and devices described herein without departing from the spirit of the present inventions or the scope of the below claims.

The invention claimed is:

1. A method for implanting a selected femoral implant into a femoral medullary canal, the method comprising:
   (1) selecting a femoral implant for implantation into the femoral medullary canal from a pre-made set of femoral implants comprising a plurality of femoral implants, wherein each femoral implant in the set includes:
      an upper portion and an insertion portion, the insertion portion including a longitudinal axis, a tip, an insertion portion anterior face, an insertion portion medial face and an insertion portion lateral face;
      an osteotomy point forming a physical discontinuity between the upper portion and the insertion portion medial face, the osteotomy point located a predetermined distance from the tip, the predetermined distance from the osteotomy point to the tip defining an insertion portion length;
      the insertion portion medial face and the insertion portion lateral face located a predetermined insertion portion width from each other at a point located twenty millimeters distal to the osteotomy point on the insertion portion medial face;
   at least some of the femoral implants in the set having an insertion portion length that differs from the insertion portion lengths of other femoral implants in the set;
   at least some of the femoral implants in the set having an insertion portion width that differs from the insertion portion widths of other femoral implants in the set;
   wherein the femoral implants in the set are configured such that curved portions of their insertion portion medial faces between their osteotomy point and a point located eighty millimeters distal to the osteotomy point are congruent in shape and length when the femoral implants are aligned such that the longitudinal axes of the insertion portions are parallel;
   (2) implanting the selected femoral implant.

2. The method of claim 1 wherein the step of selecting a femoral implant for implantation into the femoral medullary canal from a pre-made set of femoral implants comprising a plurality of femoral implants includes selecting a femoral implant from the set wherein the insertion portion medial face and the insertion portion lateral face of each femoral implant in the set defines an insertion portion taper angle, and all implants in the set have the same insertion portion taper angle.

3. The method of claim 1 wherein the step of selecting a femoral implant for implantation into the femoral medullary canal from a pre-made set of femoral implants comprising a plurality of femoral implants includes selecting a femoral implant from the set wherein the ratio of percentage change in insertion portion length to percentage change in insertion portion width between any two femoral implants in the set does not equal one.

4. The method of claim 1 wherein the step of selecting a femoral implant for implantation into the femoral medullary canal from a pre-made set of femoral implants comprising a plurality of femoral implants includes selecting a femoral implant from the set wherein a portion of the insertion portion medial face of each implant has a constant medial face portion radius of curvature, and all implants in the set have the same constant medial face portion radius of curvature.

5. The method of claim 1, wherein the step of selecting a femoral implant for implantation further comprises selecting a femoral implant for implantation wherein each femoral implant in the set includes the insertion portion medial face and the insertion portion lateral face located a predetermined insertion portion distal width from each other at a point located eighty millimeters distal to the osteotomy point on the insertion portion medial face, wherein at least some of the femoral implants in the set having an insertion portion distal width that differs from the insertion portion distal widths of other femoral implants in the set.

6. A method for implanting a selected femoral implant into a femoral medullary canal, the method comprising:
(1) selecting a femoral implant for implantation into the femoral medullary canal from a pre-made set of femoral implants comprising a plurality of femoral implants, wherein each femoral implant in the set includes:
an upper portion and an insertion portion, the insertion portion including a longitudinal axis, a tip, an insertion portion anterior face, an insertion portion medial face and an insertion portion lateral face, the insertion portion including a bone interface surface adapted to abut bone into which the insertion portion is inserted;
an osteotomy point forming a promontory located between the implant upper portion and the insertion portion medial face, the osteotomy point located a predetermined distance from the tip, the predetermined distance from the osteotomy point to the tip defining an insertion portion length;
the insertion portion medial face and the insertion portion lateral face located a predetermined insertion portion width from each other at a point located twenty millimeters distal to the osteotomy point on the insertion portion medial face;
at least some of the femoral implants in the set having an insertion portion length that differs from the insertion portion lengths of other femoral implants in the set;
at least some of the femoral implants in the set having an insertion portion width that differs from the insertion portion widths of other femoral implants in the set;
wherein the femoral implants in the set are configured such that curved portions of their insertion portion medial faces between their osteotomy point and a point located eighty millimeters distal to the osteotomy point are congruent in shape and length when the femoral implants are aligned such that the longitudinal axes of the insertion portions are parallel;
(2) implanting the selected femoral implant.

7. The method of claim 6 wherein the step of selecting a femoral implant for implantation into the femoral medullary canal from a pre-made set of femoral implants comprising a plurality of femoral implants includes selecting a femoral implant from the set wherein the insertion portion medial face and the insertion portion lateral face of each femoral implant in the set defines an insertion portion taper angle, and all implants in the set have the same insertion portion taper angle.

8. The method of claim 6 wherein the step of selecting a femoral implant for implantation into the femoral medullary canal from a pre-made set of femoral implants comprising a plurality of femoral implants includes selecting a femoral implant from the set wherein the ratio of percentage change in insertion portion length to percentage change in insertion portion width between any two femoral implants in the set does not equal one.

9. The method of claim 6 wherein the step of selecting a femoral implant for implantation into the femoral medullary canal from a pre-made set of femoral implants comprising a plurality of femoral implants includes selecting a femoral implant from the set wherein a portion of the insertion portion medial face of each implant has a constant medial face portion radius of curvature, and all implants in the set have the same constant medial face portion radius of curvature.

10. The method of claim 6, wherein the step of selecting a femoral implant for implantation further comprises selecting a femoral implant for implantation wherein each femoral implant in the set includes the insertion portion medial face and the insertion portion lateral face located a predetermined insertion portion distal width from each other at a point located eighty millimeters distal to the osteotomy point on the insertion portion medial face, wherein at least some of the femoral implants in the set having an insertion portion distal width that differs from the insertion portion distal widths of other femoral implants in the set.

11. A method for implanting a selected femoral implant into a femoral medullary canal, the method comprising:
(1) selecting a femoral implant for implantation into the femoral medullary canal from a pre-made set of femoral implants comprising a plurality of femoral implants, wherein each femoral implant in the set includes:
an upper portion and an insertion portion, the insertion portion including a longitudinal axis, a tip, an insertion portion anterior face, an insertion portion medial face and an insertion portion lateral face;
an osteotomy point forming a promontory located between the upper portion and the insertion portion medial face, the osteotomy point located a predetermined distance from the tip, the predetermined distance from the osteotomy point to the tip defining an insertion portion length;
the insertion portion medial face and the insertion portion lateral face defining an insertion portion taper angle;
the insertion portion medial face and the insertion portion lateral face located a predetermined insertion portion width from each other at a point located twenty millimeters distal to the osteotomy point on the insertion portion medial face;
at least some of the femoral implants in the set having an insertion portion length that differs from the insertion portion lengths of other femoral implants in the set;
at least some of the femoral implants in the set having an insertion portion width that differs from the insertion portion widths of other femoral implants in the set;
at least some of the femoral implants in the set having the same insertion portion taper angle as the other femoral implants in the set;
wherein the ratio of percentage change in insertion portion length to percentage chance in insertion portion width between any two femoral implants in the set does not equal one; and
wherein the femoral implants in the set are configured such that curved portions of their insertion portion medial faces between their osteotomy point and the point located twenty millimeters distal to the osteotomy point are congruent in shape and length when the femoral implants are aligned such that the longitudinal axes of the insertion portions are parallel;
(2) implanting the selected femoral implant;
wherein the step of selecting a femoral implant for implantation further comprises selecting a femoral implant for implantation wherein each femoral implant in the set includes the insertion portion medial face and the insertion portion lateral face located a predetermined insertion portion distal width from each other at a point located eighty millimeters distal to the osteotomy point on the insertion portion medial face, wherein at least some of the femoral implants in the set having an insertion portion distal width that differs from the insertion portion distal widths of other femoral implants in the set.

* * * * *